United States Patent
Appling et al.

(10) Patent No.: US 7,273,478 B2
(45) Date of Patent: Sep. 25, 2007

(54) ENDOVASCULAR TREATMENT DEVICE HAVING A FIBER TIP SPACER

(75) Inventors: William M. Appling, Granville, NY (US); Eamonn Hobbs, Queensbury, NY (US)

(73) Assignee: AngioDynamics, Inc., Queensbury, NY (US)

( * ) Notice: Subject to any disclaimer, the term of this patent is extended or adjusted under 35 U.S.C. 154(b) by 0 days.

(21) Appl. No.: 10/613,395

(22) Filed: Jul. 3, 2003

(65) Prior Publication Data

US 2004/0010248 A1 Jan. 15, 2004

Related U.S. Application Data

(60) Provisional application No. 60/395,218, filed on Jul. 10, 2002.

(51) Int. Cl.
*A61B 18/18* (2006.01)
*A61B 18/20* (2006.01)

(52) U.S. Cl. .............................. 606/15; 606/7; 128/898

(58) Field of Classification Search .................. 606/7, 606/15, 16; 607/88, 89; 128/898
See application file for complete search history.

(56) References Cited

U.S. PATENT DOCUMENTS

| | | | | | |
|---|---|---|---|---|---|
| 4,817,601 | A | * | 4/1989 | Roth et al. ...................... | 606/7 |
| 5,026,366 | A | * | 6/1991 | Leckrone ........................ | 606/7 |
| 5,188,635 | A | * | 2/1993 | Radtke .......................... | 606/14 |
| 5,445,608 | A | * | 8/1995 | Chen et al. .................... | 604/20 |
| 5,643,253 | A | * | 7/1997 | Baxter et al. .................. | 606/17 |
| 5,693,043 | A | * | 12/1997 | Kittrell et al. ................. | 606/15 |
| 5,725,521 | A | * | 3/1998 | Mueller .......................... | 606/7 |
| 6,033,398 | A | * | 3/2000 | Farley et al. .................. | 606/27 |
| 6,344,048 | B1 | * | 2/2002 | Chin et al. .................... | 606/200 |
| 6,398,777 | B1 | | 6/2002 | Navarro et al. | |
| 6,561,998 | B1 | * | 5/2003 | Roth et al. ..................... | 604/22 |
| 6,767,338 | B2 | * | 7/2004 | Hawk et al. ........... | 604/164.01 |
| 6,986,766 | B2 | * | 1/2006 | Caldera et al. ............... | 606/15 |

FOREIGN PATENT DOCUMENTS

EP   0 311 295 A2  *  4/1989
EP   0311295 A2       4/1989

OTHER PUBLICATIONS

Exhibit A: "Vari Lase," Endovenous Laser Procedure Kit, Vascular Solutions, 2003.*
Exhibit B: DUETT Sealing Device, Model 1000, Vascular Solutions, 1999.*
Min et al., "Endovenous Laser Treatment of Saphenous Vein Reflux: Long-Trerm Results," Aug. 2003, JVIR.*
The ClosureO Procedure Physician Self Course.*
"Endovenous Treatment of the Greater Saphenous Vein with a 940-nm Diode Laser: Thrombotic Occlusion After Endoluminal Thermal Damage By Laser-Generated Steam Bubble" by T. M. Proebstle, MD, in Journal of Vascular Surgery, vol. 35, pp. 729-736 (Apr. 2002).
"Thermal Damage of the Inner Vein Wall During Endovenous Laser Treatment: Key Role of Energy Absorption by Intravascular Blood" by T. M. Proebstle, MD, in Dermatol Surg, vol. 28, pp. 596-600 (2002).

* cited by examiner

*Primary Examiner*—A. Farah
(74) *Attorney, Agent, or Firm*—Reed Smith LLP

(57) ABSTRACT

An endovascular laser treatment device designed to be used with an optical fiber to treat venous diseases such as varicose veins is provided. The device includes a spacer that positions the distal end of the optical fiber away from the inner wall of the blood vessel during delivery of laser energy to provide an even distribution of thermal energy around the vessel, thereby avoiding vessel perforation and incomplete vessel collapse.

5 Claims, 8 Drawing Sheets

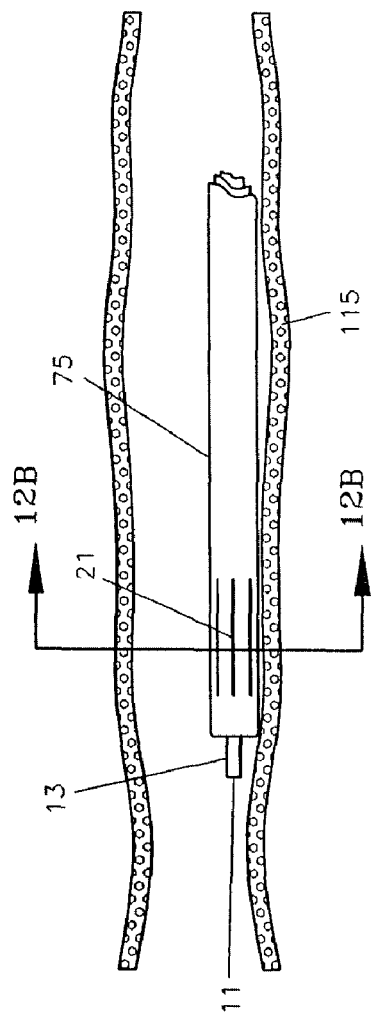
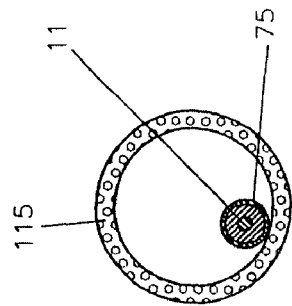
FIG. 12A
FIG. 12B
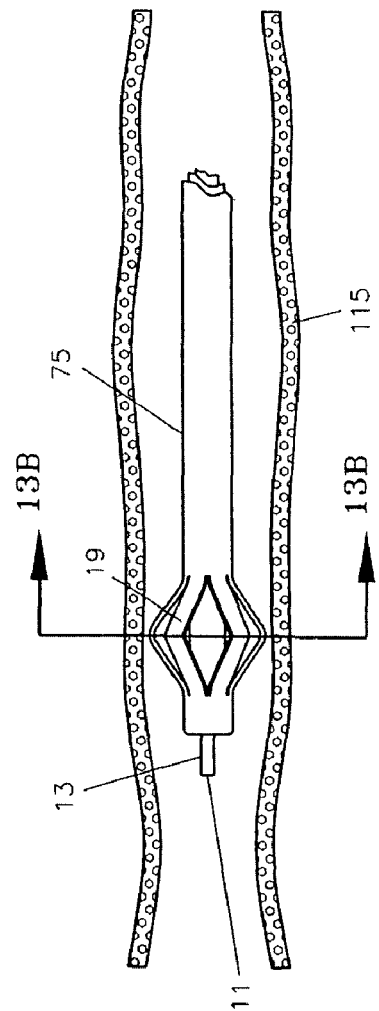
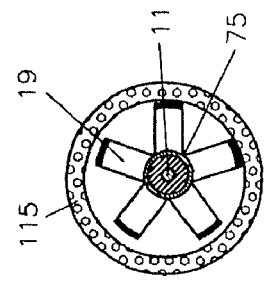
FIG. 13A
FIG. 13B

ENDOVASCULAR TREATMENT DEVICE HAVING A FIBER TIP SPACER

CROSS REFERENCE TO RELATED APPLICATIONS

This application claims priority under 35 U.S.C. §119 (e) to U.S. provisional application, Ser. No. 60/395,218, filed Jul. 10, 2002, the disclosure of which is hereby incorporated by reference.

FIELD OF THE INVENTION

The present invention relates to a medical device apparatus and method for treatment of blood vessels. More particularly, the present invention relates to a laser fiber device and method for endovenous thermal treatment of varicose veins.

BACKGROUND OF THE INVENTION

Veins are thin-walled and contain one-way valves that control blood flow. Normally, the valves open to allow blood to flow into the deeper veins and close to prevent back-flow into the superficial veins. When the valves are malfunctioning or only partially functioning, however, they no longer prevent the back-flow of blood into the superficial veins. As a result, venous pressure builds at the site of the faulty valves. Because the veins are thin walled and not able to withstand the increased pressure, they become what are known as varicose veins which are veins that are dilated, tortuous or engorged.

In particular, varicose veins of the lower extremities is one of the most common medical conditions of the adult population. It is estimated that varicose veins affect approximately 25% of adult females and 10% of males. Symptoms include discomfort, aching of the legs, itching, cosmetic deformities, and swelling. If left untreated, varicose veins may cause medical complications such as bleeding, phlebitis, ulcerations, thrombi and lipodermatosclerosis.

Traditional treatments for varicosities include both temporary and permanent techniques. Temporary treatments involve use of compression stockings and elevation of the diseased extremities. While providing temporary relief of symptoms, these techniques do not correct the underlying cause, that is the faulty valves. Permanent treatments include surgical excision of the diseased segments, ambulatory phlebectomy, and occlusion of the vein through chemical or thermal means.

Surgical excision requires general anesthesia and a long recovery period. Even with its high clinical success rate, surgical excision is rapidly becoming an outmoded technique due to the high costs of treatment and complication risks from surgery. Ambulatory phlebectomy involves avulsion of the varicose vein segment using multiple stab incisions through the skin. The procedure is done on an outpatient basis, but is still relatively expensive due to the length of time required to perform the procedure.

Chemical occlusion, also known as sclerotherapy, is an in-office procedure involving the injection of an irritant chemical into the vein. The chemical acts upon the inner lining of the vein walls causing them to occlude and block blood flow. Although a popular treatment option, complications can be severe including skin ulceration, anaphylactic reactions and permanent skin staining. Treatment is limited to veins of a particular size range. In addition, there is a relatively high recurrence rate due to vessel recanalization.

Endovascular laser therapy is a relatively new treatment technique for venous reflux diseases. With this technique, the laser energy is delivered by a flexible optical fiber that is percutaneously inserted into the diseased vein prior to energy delivery. An introducer catheter or sheath is typically first inserted into the saphenous vein at a distal location and advanced to within a few centimeters of the saphenous-femoral junction of the greater saphenous vein. Once the sheath is properly positioned, a flexible optical fiber is inserted into the lumen of the sheath and advanced until the fiber tip is near the sheath tip but still protected within the sheath lumen.

Prior to laser activation, the sheath is withdrawn approximately 1-4 centimeters to expose the distal tip of the optical fiber. After the fiber tip has been exposed the correct distance beyond the sheath tip, a laser generator is activated causing laser energy to be emitted from the bare flat tip of the fiber into the vessel. The energy contacts the blood causing hot bubbles of gas to be created. The gas bubbles transfer thermal energy to the vein wall, causing cell necrosis and eventual vein collapse. With the laser generator turned on, the optical fiber and sheath are slowly withdrawn as a single unit until the entire diseased segment of the vessel has been treated.

A typical laser system uses a 600-micron optical fiber covered with a thick polymer jacket. The fiber extends unprotected from the polymer jacket, approximately 4 mm in length at the tip of the optical fiber. The fiber's tip is ground and polished to form a flat face at its extreme distal end. The flat face is necessary to ensure energy is directed in a forward direction rather than radially, which would occur if the fiber tip configuration were radiused. The flat face of the optical fiber tip directs the laser energy from the fiber to the vein's lumen rather than directly to the vein walls.

With prior art treatment methods, contact between the energy-emitting face of the fiber optic tip and the inner wall of the varicose vein is recommended to ensure complete collapse of the diseased vessel. In U.S. Pat. No. 6,398,777, Navarro et al, teaches either the means of applying pressure over the laser tip or emptying the vessel of blood to ensure that there is contact between the vessel wall and the fiber tip.

One problem with direct contact between the laser fiber tip and the inner wall of the vessel is that it can result in vessel perforation and extravasation of blood into the perivascular tissue. This problem is documented in numerous scientific articles including "Endovenous Treatment of the Greater Saphenous Vein with a 940-nm Diode Laser: Thrombotic Occlusion After Endoluminal Thermal Damage By Laser-Generated Steam Bubble" by T. M. Proebstle, MD, in Journal of Vascular Surgery, Vol. 35, pp. 729-736 (April, 2002), and "Thermal Damage of the Inner Vein Wall During Endovenous Laser Treatment: Key Role of Energy Absorption by Intravascular Blood" by T. M. Proebstle, MD, in Dermatol Surg, Vol. 28, pp. 596-600 (2002), both of which are incorporated herein by reference. When the fiber contacts the vessel wall during treatment, intense direct laser energy is delivered to the vessel wall rather than indirect thermal energy created as the blood is converted into gas bubbles. Laser energy in direct contact with the vessel wall causes the vein to perforate at the contact point and surrounding area. Blood escapes through these perforations into the perivascular tissue, resulting in post-treatment bruising and associated discomfort.

Another problem created by the prior art methods involving contact between the fiber tip and vessel wall is that inadequate energy is delivered to the non-contact segments of the diseased vein. Inadequately heated vein tissue may not necrose or collapse, resulting in incomplete treatment. With the fiber tip in contact with the vessel wall rather than the bloodstream, hot gas bubbles are not created. The bubble is the mechanism by which the 360 degree circumference of the vessel wall is damaged. Without the bubbles, it is possible for some vein tissue to be under heated or not heated at all, resulting in incomplete treatment and possible recanalization of the vessel.

Therefore, it is desirable to provide an endovascular treatment device and method which protects the optical fiber tip from direct contact with the inner wall of vessel during the emission of laser energy to ensure consistent thermal heating across the entire vessel circumference thus avoiding vessel perforation or incomplete vessel collapse.

SUMMARY OF THE DISCLOSURE

According to the principles of the present invention, an endovascular laser treatment device adapted to be used with an optical fiber is provided. The device includes a spacer arranged near a distal end of the optical fiber. The spacer positions the distal end of the optical fiber away from the inner wall of the blood vessel during delivery of laser energy through the optical fiber. In one embodiment, the spacer is in an undeployed state while being inserted into the blood vessel. Once the undeployed spacer is inserted into the vessel, the spacer is placed into a deployed state where it positions the optical fiber end away from the inner vessel wall.

In another embodiment, the spacer is attached to the optical fiber near its distal end. The fiber is inserted into the blood vessel with the undeployed spacer attached at its end. Once, the undeployed spacer is inserted into the vessel, the spacer is placed into the deployed state. The spacer may includes a plurality of ribs which expand in a radial direction within the vessel.

In another embodiment, the spacer is separate from the optical fiber. The spacer is part of an outer tube that surrounds an inner tube. The inner tube is adapted to receive the optical fiber. The outer tube has its distal portion attached to the first tube and the spacer is arranged near the distal portion of the outer tube. The spacer is placed into the deployed state when the outer tube is moved relative to the inner tube.

In the deployed state, the spacer prevents contact between the fiber tip and the inner vessel wall to direct the laser energy forward into the vessel lumen and bloodstream in order to avoid the application of laser energy directly to the vessel wall. The laser energy applied to the blood stream creates hot gas bubbles. As the hot gas bubbles contact the vessel wall, thermal energy is transferred to the wall, causing tissue damage and ultimate collapse of the vessel. Because the spacer of the present invention positions the fiber tip away from the vessel wall, the present invention avoids the over heating or under heating of the inner vessel wall that occurs when the fiber tip comes in direct contact with the vessel.

BRIEF DESCRIPTION OF THE DRAWINGS

FIG. 12A illustrates the spacer ribs in the undeployed state within a blood vessel.

FIG. 12B is a cross sectional view taken along the line 12B-12B of FIG. 12A.

FIG. 13A illustrates the spacer ribs in the deployed state within the blood vessel.

FIG. 13B is a cross sectional view taken along the line 13B-13B of FIG. 13A.

DETAILED DESCRIPTION OF THE INVENTION

Figure 1:
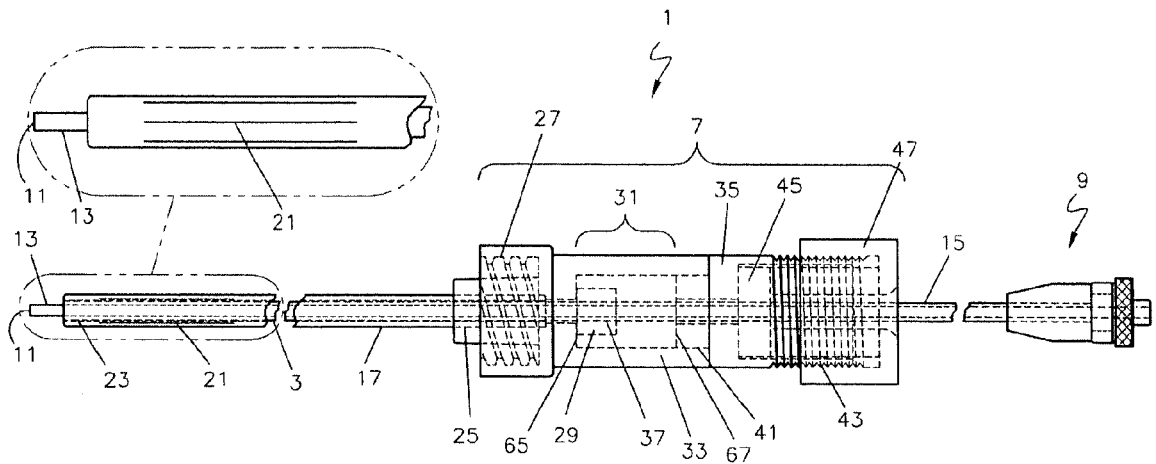
FIG. 1 is a plan view of an endovascular laser treatment device with an enlarged view of a portion of spacer ribs in an undeployed state according to the present invention.

A preferred embodiment of the present invention is shown in FIGS. 1-4C. The endovascular laser treatment device 1 shown in FIG. 1 and FIG. 2 includes an optical fiber 3 which is comprised of clad-coated fiber 13 and jacket 15. The device also includes an outer sleeve 17, fitting assembly 7, which also acts as a deployment mechanism, compression gasket 45 and a compression cap 47. The optical fiber 3 transmits the laser energy from a laser generator (not shown) into a vessel. The fitting assembly 7 acts as a deployment mechanism for a spacer element to be discussed in detail later herein. The compression gasket 45 and compression cap 47 provide a sealing function and when compressed, generate friction sufficient to maintain the position of the optical fiber 3.

As is well known in the art, the optical fiber 3 is typically comprised of a 600-micron laser fiber 13 encased in a thick polymer jacket 15 for the entire length of the fiber 3 except for approximately 4 mm at the distal end. The jacket 15 prevents the fragile fiber from breaking during use. A thin intermediate cladding (not shown) creates a barrier through which the laser energy cannot penetrate, thus causing the energy to move longitudinally through the fiber 3 to the distal end where the laser energy is emitted. At the distal end, the bare fiber 13 extends unprotected from the polymer jacket 15. The proximal end of the optical fiber 3 is connected to a SMA or similar-type connector 9, which can be attached to the laser generator (not shown). At the distal end, the optical fiber tip is ground and polished to form a flat face 11. Thus, the flat face 11 of the optical fiber 3 tip directs the laser energy from the fiber in a longitudinal direction.

The outer sleeve 17 is a tubular structure preferably comprised of a flexible, low-friction material such as nylon. The outer sleeve 17 is arranged coaxially around the optical fiber 3. For accommodation of the 600 micron optical fiber core, the outer sleeve 17 inner diameter is preferably about 0.045", although other diameters can be used for different optical fiber sizes. The outer diameter of the sleeve 17 is sized to fit within a standard 5F sheath. Typically, a sleeve 17 dimensioned with a 0.066" outer diameter should slidably fit within the lumen of a 5F sheath, which has an approximate inner diameter of 0.070".

The outer sleeve 17 is coaxially arranged around the optical fiber 3 and permanently attached to the fiber 3 at the distal end of the sleeve 17 at point 23 which defines a bonding zone between the fiber 3 and the distal end of the sleeve 17. The outer sleeve 17 can be moved longitudinally relative to the optical fiber 3 except at the point 23. The sleeve 17 includes a plurality of longitudinal slits 21 in the tubing at the distal end to define a plurality of ribs 19 each arranged between two adjacent slits. Preferably, there are three to six slits while the embodiment shown has five slits to define five ribs 19. The ribs 19 disposed near the distal tip 11 of the optical fiber 3 define a spacer element that positions the distal tip 11 away from the inner wall of the vessel. When the sleeve 17 is moved longitudinally toward the fiber tip 11 relative to the optical fiber 3, the slits 21 expand radially outward to deploy the spacer element 19, as will be explained in more detail below. At the proximal end, the sleeve 17 is permanently bonded to the distal fitting component 33 at the sleeve/fitting assembly bond point 25, as more clearly shown in FIG. 2.

A fitting assembly 7 positioned at the proximal end of the outer sleeve 17 provides the mechanism by which the spacer element 19 is moved from an undeployed to deployed position. The fitting assembly 7 is comprised of a distal fitting component 33, a proximal fitting component 35 and a compression cap 47 threadably connected to the proximal fitting component 35. In the preferred embodiment, the two fitting components 33 and 35 are permanently attached together at bond point 41.

The distal fitting component 33 includes a male luer connector 27 or other similar type connection element which functions to connect the endovascular laser treatment device 1 to other commonly used medical devices such as a hemostasis sheath. The outer sleeve shaft 17 is bonded to the male luer connector 27 of the distal fitting component 33 at point 25. The distal fitting component 33 has a longitudinal channel 39 through which the optical fiber 3 is positioned.

Figure 2:
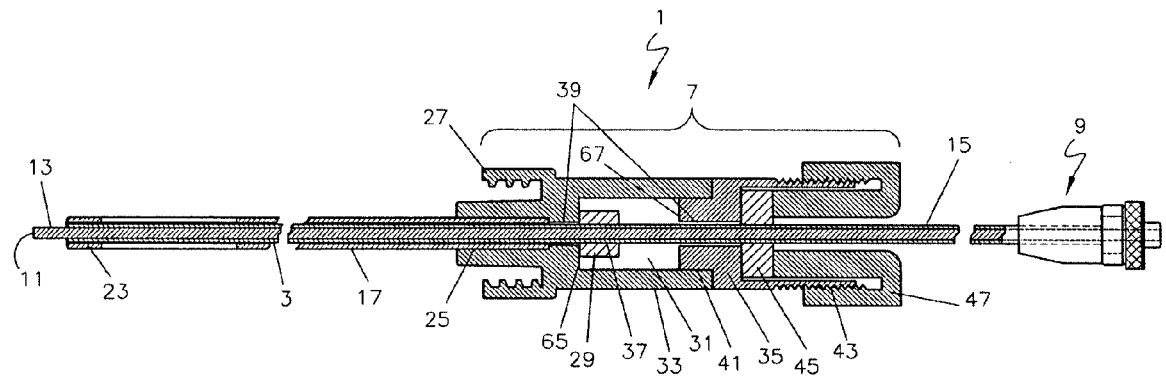
FIG. 2 is a cross-sectional view of the endovascular laser treatment device of FIG. 1.

The proximal fitting component 35 also includes a longitudinal channel 39, as shown in FIG. 2, through which the optical fiber 3 is positioned. The proximal end of the fitting component 35 includes a cavity into which a gasket 45 is positioned. The gasket 45 is made of silicone or other compressible material with a central opening through which the optical fiber 3 passes. The gasket 45 provides the dual functions of sealing the channel 39 and providing friction sufficient to maintain the longitudinal position of the optical fiber 3 within the channel 39. The gasket compression threads 43 at the proximal end of fitting component 35 provide an axially moveable connection between the fitting 35 and the compression cap 47. When the compression cap 47 is threaded into the fitting 35, the gasket 45 is compressed, thus tightening the seal and increasing the friction between the fiber 3 and the gasket 45. When the compression cap 47 is loosened relative to the compression threads 43, the gasket seal is relaxed and the friction against the optical fiber decreased.

When assembled together, the proximal fitting component 35 and the distal fitting component 33 form a hollow positioning chamber 31 as shown in FIG. 2. Within the positioning chamber 31 is a positioning element 29 that is permanently attached to the optical fiber jacket 15 at bond point 37. During deployment of the spacer element 19, the positioning element 29 provides the function of limiting the longitudinal movement of the combined fitting assembly 7/outer sleeve 17 relative to the optical fiber 3. In the undeployed position, the positioning element 29 is in contact with the distal chamber face 65. Longitudinal movement of fitting assembly causes the positioning element 29 to be repositioned within the chamber 31. Forward longitudinal movement of the fitting 7/outer sleeve 17 is stopped when the positioning element 29 comes in contact with proximal chamber face 67.

Figure 3:
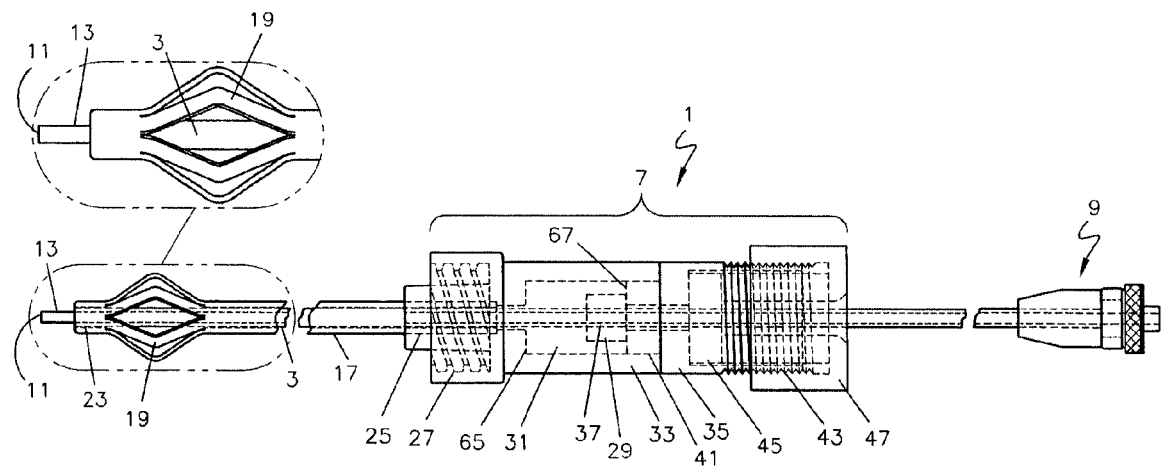
FIG. 3 is a plan view of the endovascular laser treatment device of FIG. 1 with an enlarged view of the spacer ribs in a deployed state.

When the positioning element 29 is against the proximal chamber face 67, the spacer element 19 is fully deployed as illustrated in FIG. 3. In this position, the spacer ribs 19 are expanded radially outward, forming a space barrier between the fiber tip 11 and the inner vein wall. The mechanism for expansion is based on the forward longitudinal movement of the outer sleeve 17 proximal to the fiber/sleeve distal bond point 23. Since the optical fiber 3 is held stationary during deployment, and the fiber is permanently bonded to the sleeve 17 at point 23, the portion of the sleeve 17 within the slit zone expands as the sleeve is pushed forward. The device 1 is designed to allow expansion of the slit zone to a maximum predetermined diameter. Alternatively, an intermediate expansion diameter can be achieved by controlling the amount of longitudinal movement within the chamber 31.

According to the invention, the spacer element 19 provides several important advantages among others. In an undeployed position, as shown in FIGS. 1 and 2, the outer diameter and profile of the spacer element 19 is equal to the outer sleeve 17, allowing for easy insertion and positioning within the vein. The fitting assembly 7 provides the user with an easy, simple means for deploying the spacer element 19 while maintaining the position of the fiber tip 11 stationary within the vein. When deployed, the spacer element 19 creates a barrier between the fiber tip 11 and the inner vein wall, thereby minimizing unequal laser energy distribution.

The preferred embodiment of this invention as illustrated in FIGS. 1-3 may be used with a standard hemostasis introducer sheath. Endovenous laser sheaths are typically 45 centimeters in length, although 60 and 65 centimeter sheaths are also well known in the art. The length of the endovascular laser treatment device 1 is determined based on the length of the sheath being used for the procedure. According to the invention, the endovascular laser treatment device 1 can be sized to fit standard-length sheaths or custom-length sheaths. Further, the assembly 1 can be provided by itself or in a package that includes either the standard length sheath or custom-length sheath.

Figure 4A:
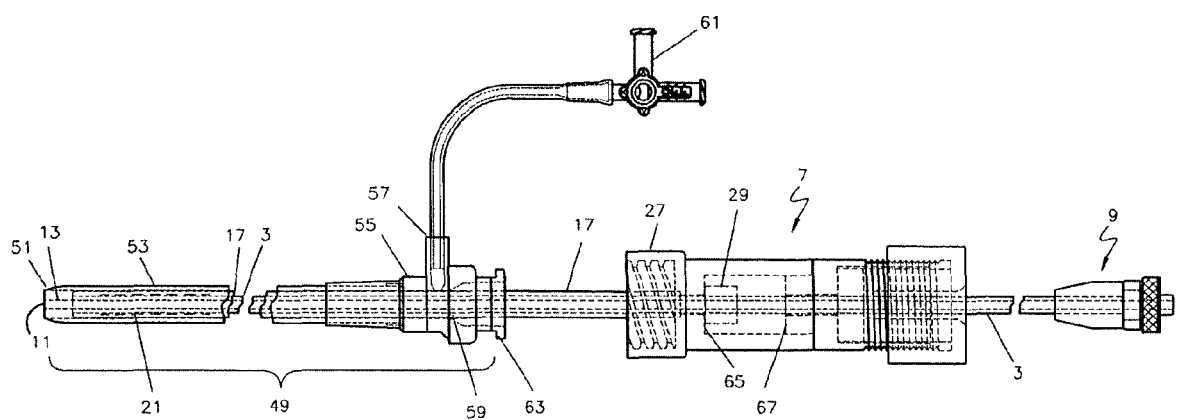
FIG. 4A is a plan view of the endovascular laser treatment device of FIG. 1 inserted into and protected within a hemostasis sheath.
Figure 4B:
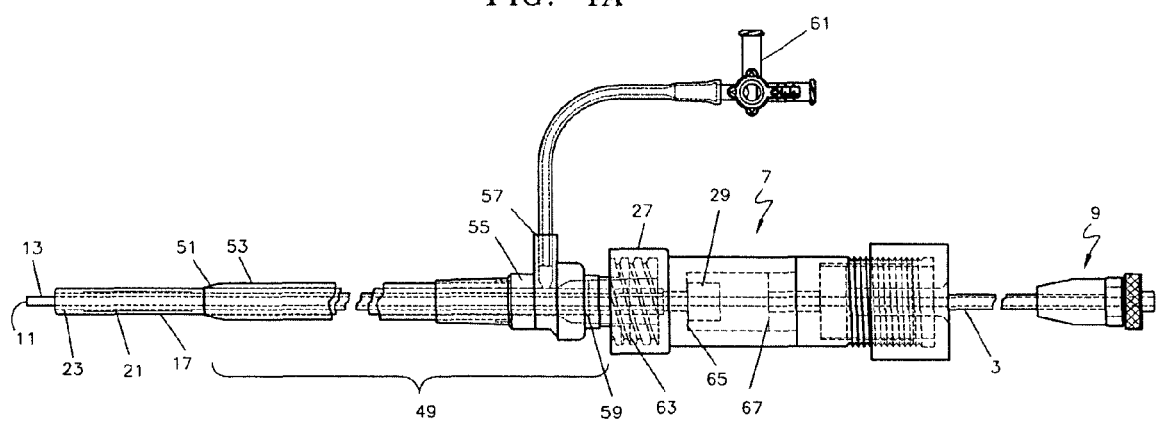
FIG. 4B is a plan view of the endovascular laser treatment device of FIG. 1 coupled with the hemostasis sheath with the spacer ribs in the undeployed state.
Figure 4C:
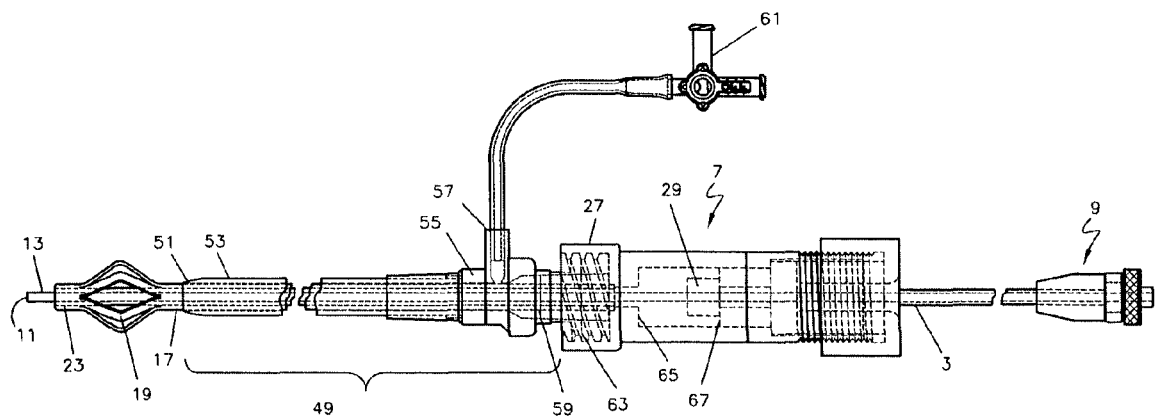
FIG. 4C is a plan view of the endovascular laser treatment device and sheath of FIG. 4B with the spacer ribs in the deployed state.

FIGS. 4A-4C show the endovascular laser treatment device 1 with a hemostasis introducer sheath 49. As is known in the art, the hemostasis introducer sheath assembly 49 is comprised of a sheath shaft 53, a sheath distal tip 51, a esidearm port 57 with connecting tubing, a stopcock assembly 61, and a hemostasis valve gasket 59 housed within proximal opening of the sheath fitting 55. A connector element 63 provides a means to connect the hemostasis sheath assembly 49 to the endovascular laser treatment device 1.

To assemble the endovascular laser treatment device 1 to the hemostasis introducer sheath 49, the fiber tip 11/outer sleeve 17 tip is first inserted into and advanced through the sheath connector element 63 and sheath shaft 53 lumen until the sheath tip 51 and fiber tip 11 are in substantial alignment as shown in FIG. 4A. At this point, with the fiber tip 11 protected within the sheath tip 51, the user may adjust the position of the combined laser treatment device 1 and sheath 49. Maintaining the fiber tip 11 position relative to the sheath tip 51 position during any user adjustments may be facilitated by the use of a temporary stop (not shown) slidably connected to the fiber 3. The temporary stop mechanism was previously disclosed in U.S. patent application Ser. No. 10/316,545, filed Dec. 11, 2002 and entitled "Endovascular Laser Treatment Device", which is incorporated herein by reference. The temporary stop maintains the fiber tip 11/sheath tip 51 alignment in a protective position until removed by the user.

To expose the fiber tip 11 and spacer element 19 beyond the sheath tip 51, the sheath fitting 55 is retracted while holding the fiber 3 stationary. Retracting the sheath fitting 55 rather than advancing the fiber 3 ensures that the correct pre-operative fiber tip 11/spacer element 19 position is maintained. The sheath fitting 55 is retracted until the sheath connector element 63 comes into contact with the male luer connector 27. Threading the two connectors 27 and 63 together securely connects the endovascular laser treatment device 1 to the hemostasis introducer sheath assembly 49. Once connected, the fiber tip 11 and spacer element 19 are automatically exposed in the proper operable position. A dual-thread arrangement, commonly used in medical devices, is shown in FIG. 4B, but other methods of connection may be used to connect the two fittings together.

FIG. 4B shows the endovascular laser treatment device 1/hemostasis introducer sheath 49 connected with the spacer element 19 in the exposed and undeployed position. In the undeployed position, the distal segment of the outer sleeve shaft 17 extends beyond the sheath tip 51 enough to completely expose the length of the slits 21. To deploy the spacer element 19, the optical fiber is held stationary while the connected sheath fitting 55/fitting assembly 7 is advanced forward. Longitudinal movement of connected fittings 55 and 7 cause the positioning element 29 to be repositioned within the chamber 31. Forward longitudinal movement of the fitting 7/outer sleeve 17 is stopped when the positioning element 29 comes in contact with proximal chamber face 67. When the positioning element 29 is against the proximal chamber face 67, the spacer element 19 is fully deployed as illustrated in FIG. 4C. In this position, the spacer ribs 19 are expanded radially outward, forming a space barrier between the fiber tip 11 and the inner vein wall.

Figure 5:
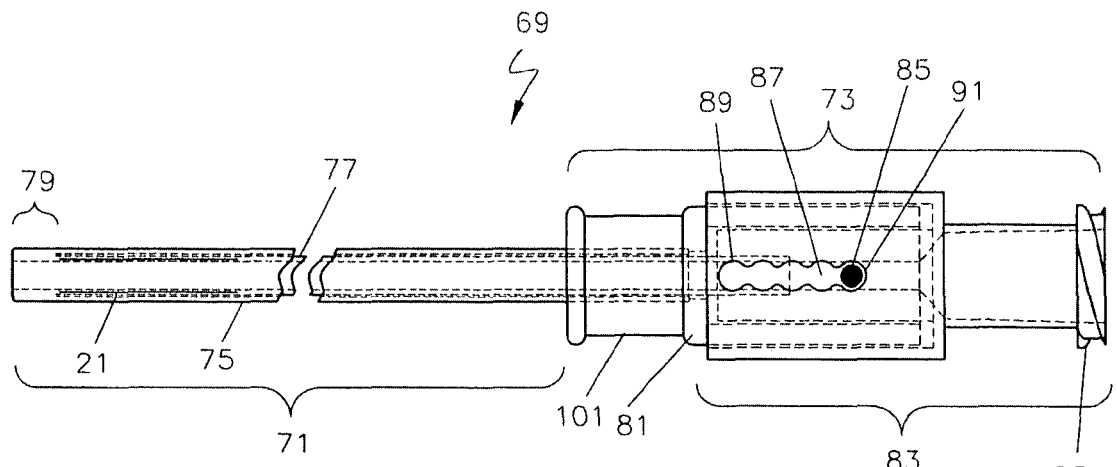
FIG. 5 is a plan view of a coaxial expanding tip sheath showing the spacer ribs in the undeployed state.
Figure 6:
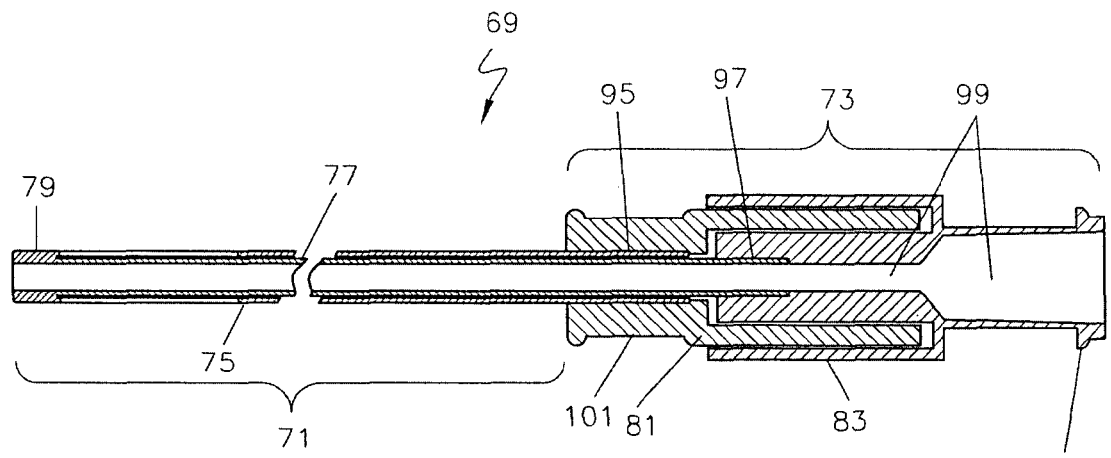
FIG. 6 is a cross-sectional view of the coaxial expanding tip sheath of FIG. 5.
Figure 7:
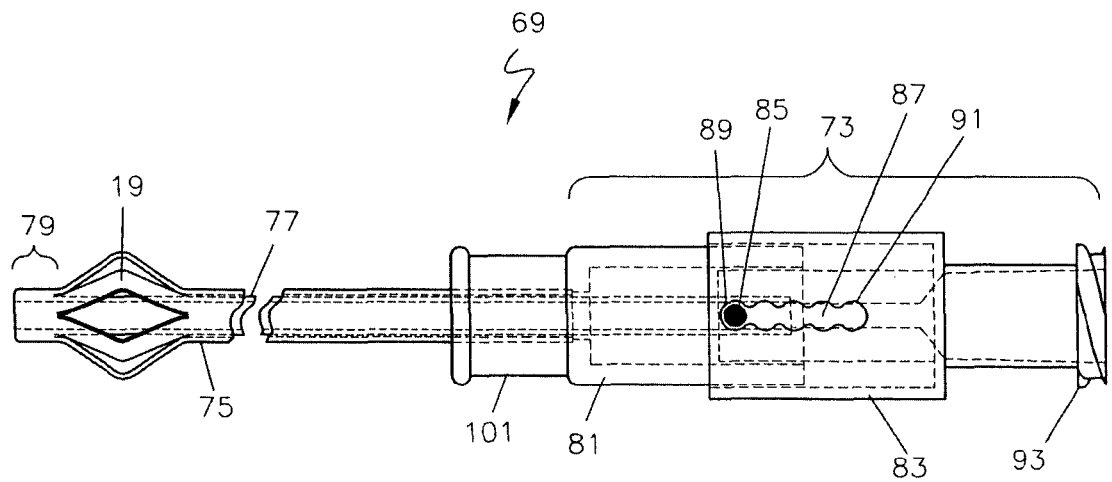
FIG. 7 is a plan view of the coaxial expanding tip sheath of FIG. 5 with the spacer ribs in the deployed state.

An alternative embodiment of endovascular laser treatment device is illustrated in FIGS. 5-7. FIG. 5 depicts a coaxial expanding tip sheath 69 designed for use with a standard laser optical fiber 3 (not shown). The coaxial expanding tip sheath is comprised of a coaxial sleeve 71, and a deployment fitting assembly 73. A through lumen 99 (see FIG. 6) extends longitudinally through the sheath 69.

The coaxial sleeve 71 consists of an outer sleeve or tube 75 and inner sleeve or tube 77 permanently connected at the distal end by an outer/inner sleeve fuse section 79. Standard welding/melting methods may be used to permanently fuse the two sleeves together at the fuse section 79. The two sleeves are slideable relative to each other, except at the fuse section 79.

Turning now to the deployment fitting assembly 73, the fitting is comprised of a distal fitting component 81 and a proximal fitting component 83. The two components are slidably connected with each other. Specifically, the distal fitting component 81 is in coaxial arrangement with the proximal fitting component 83, allowing for longitudinal movement between the two components relative to each other. Gripping surface 101 of distal fitting component 81 may be used to facilitate longitudinal movement between the two components. Both deployment fittings 81 and 83 include a through lumen 99, through which the optical fiber 3 (not shown) may be inserted.

Now referring to FIG. 6, the outer sleeve 75 of the coaxial sleeve 71 is securely attached to the distal fitting component 81 at connection point 95. On the other hand, the inner sleeve 77 of coaxial sleeve 71 is securely attached to the proximal fitting component 83 at connection point 97. Proximal fitting component 83 includes a standard female luer connector 93 that is connectable to the male luer fiber connector 103 shown in FIG. 8 and described in more detail below.

The proximal fitting component 83 includes a longitudinally positioned multiple detent slot 87, as shown in FIG. 5 and FIG. 7. A pin 85 attached to the distal fitting component 81 slides longitudinally within the detent slot 87 of the proximal fitting component 83. FIG. 5 shows the coaxial expanding tip sheath 69 with the deployment fitting assembly 73 in the undeployed position, as indicated by the position of pin 85. When pin 85 is in the proximal detent position 91, the sheath 69 is in an undeployed configuration.

To deploy the spacer element 19, the distal fitting component 81 is gripped along gripping surface 101 and pushed distally while holding the proximal fitting component 83 stationary. The longitudinal forward movement of the distal fitting component 81 causes pin 85 to move within slot 87 from proximal detent position 91 to distal detent position 89, as depicted in FIG. 7. This movement also causes the outer sleeve 75 to slide distally since it is securely attached to the distal fitting component 81 at bond 95. The inner sleeve 77, on the other hand, does not move as it is securely attached to the stationary proximal fitting component 83 at bond 97. The combined movement of the outer sleeve 75 and the fixed position of the inner sleeve 77 cause the ribs 19 to expand radially outward into a deployed position as shown in FIG. 7.

The intermediate detent positions in slot 87 may be used to control the extent of expansion of the spacer element 19. This feature allows varying diameter veins to be treated with the same device. For example, positioning the pin 85 as described above to the detent position just distal of detent position 91 will expand the rib elements 19 only slightly. Positioning the pin 85 in more distal detent positions will cause further expansion of the rib elements 19. The ribs 19 are at the maximum expanded state when the pin is in detent position 89.

Figure 8:
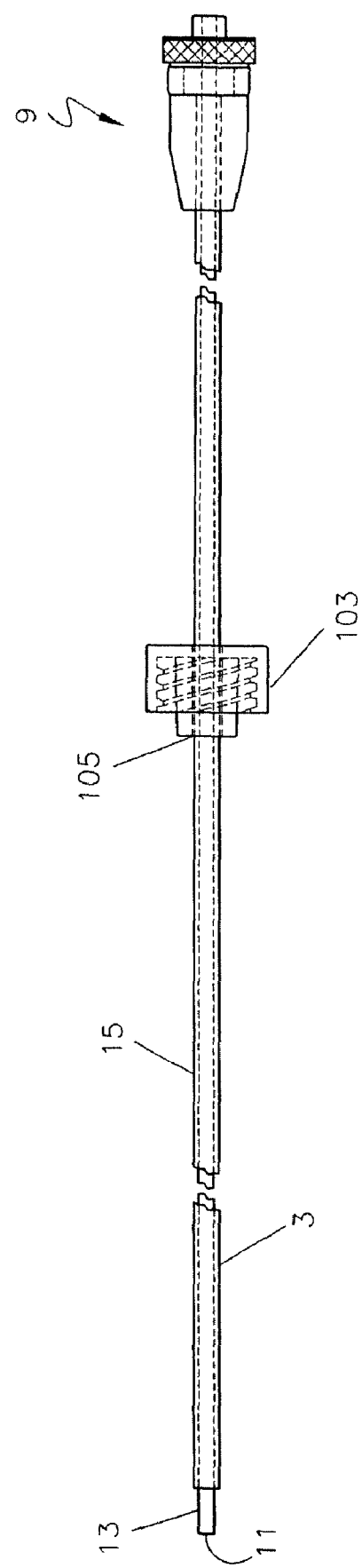
FIG. 8 is a plan view of the optical fiber with a male luer fiber connector.

FIG. 8 depicts an optical fiber assembly modified for use with the coaxial expanding tip sheath embodiment of FIG. 5 to FIG. 7. This optical fiber embodiment was previously disclosed in U.S. patent application Ser. No. 10/316,545, filed Dec. 11, 2002 entitled "Endovascular Laser Treatment Device" and is hereby incorporated by reference. The optical fiber assembly of FIG. 8 comprises an optical fiber 13, 15, a standard SMA connector 9 for connection to a laser generator (not shown), and a male luer fiber connector 103 bonded to the optical fiber 3 at connector/fiber bond point 105. Approximately 2-4 mm of the optical fiber 3 distal end is bare fiber 13 with cladding. Fiber optic tip is identified as 11. In a preferred embodiment, the male luer connector 103 includes a through-hole through which the fiber 3 passes and through which the fiber 3 is bonded to the connector 103 at bond point 105.

Figure 9:
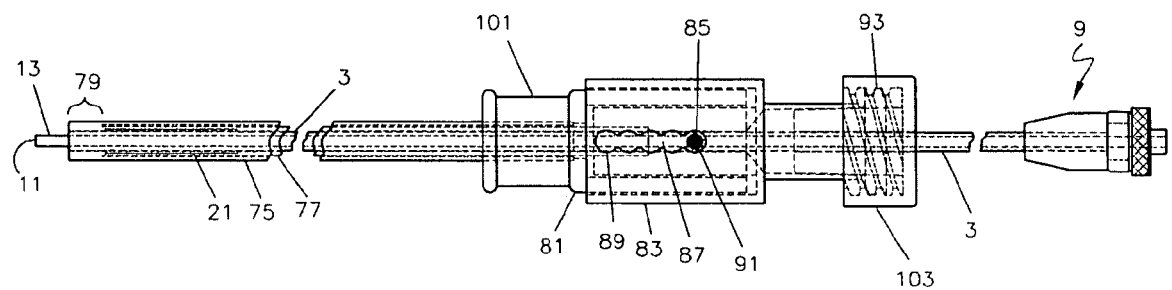
FIG. 9 is a plan view of the coaxial expanding tip sheath of FIG. 5 assembled with the optical fiber of FIG. 8.
Figure 10:
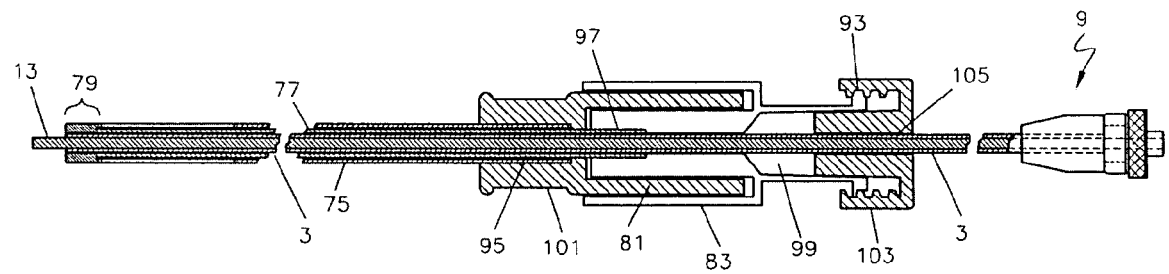
FIG. 10 is a partial cross-sectional view of assembly shown in FIG. 9.
Figure 11:
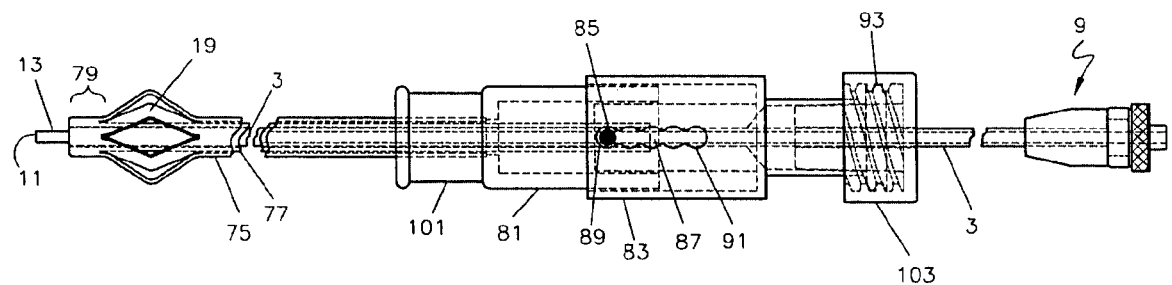
FIG. 11 is a plan view of the coaxial expanding tip sheath assembly shown in FIG. 9 with the spacer ribs in the deployed state.

FIGS. 9 and 10 illustrate the coaxial expanding tip sheath embodiment coupled to an optical fiber of FIG. 8 in an undeployed configuration. The fiber 3 can be inserted and positioned as shown in FIG. 9 prior to insertion of the device or after the coaxial expanding tip sheath 69 has been placed within the vein. To insert and connect the optical fiber 3 into the sheath 69, the distal tip 11 of the fiber is inserted and advanced through common lumen 99 (FIG. 6) of the proximal fitting component 83, distal fitting component 81 lumen 99 and inner sleeve lumen, and the two luer connectors are locked with each other to securely attach the fiber 3 to the sheath 69.

When the fiber 3 is locked into position with the sheath 69 with the spacer ribs 19 in the undeployed state, the outer tube 75 is positioned within the blood vessel 115 as shown in FIGS. 12A and 12B. When the spacer ribs 19 are in the deployed state within the vessel 115, the expanded spacer ribs 19 position the fiber tip 11 away from the inner wall of the vessel as shown in FIGS. 13A and 13B. As depicted in FIG. 13B, the spacer ribs 19 do not have to be centered within the vessel lumen. The spacer ribs 19 can be deployed such that only some of the ribs contact the inner vessel wall and still provide sufficient space to prevent the fiber tip 11 from directly contacting the vessel wall.

The expanding tip sheath 69 embodiment is advantageous in several respects. The single device functions as both an introducer sheath and a spacer device for the fiber tip. As such, the size of the overall device is smaller in diameter than if separate components were used in the procedure. Accordingly, the size of the access puncture is smaller and less traumatic to the patient. The expanding tip sheath 69 is independent of the optical fiber 3 allowing separate placement and withdrawal of the fiber, if desired. This embodiment also allows the introduction of diagnostic and interventional devices and fluids through the sheath lumen 99. For example, the sheath 69 can be optionally inserted directly over a standard guidewire as part of the placement and positioning step. Saline or other procedural fluids can be introduced through the sheath lumen 99 into the vein. The fitting assembly 73 provides the user with an easy, simple means for deploying the spacer element 19 while maintaining the position of the fiber tip 11 stationary within the vein. When deployed, the spacer element 19 creates a barrier between the fiber tip 11 and the inner vein wall whereby minimizing unequal laser energy distribution.

Figure 14:
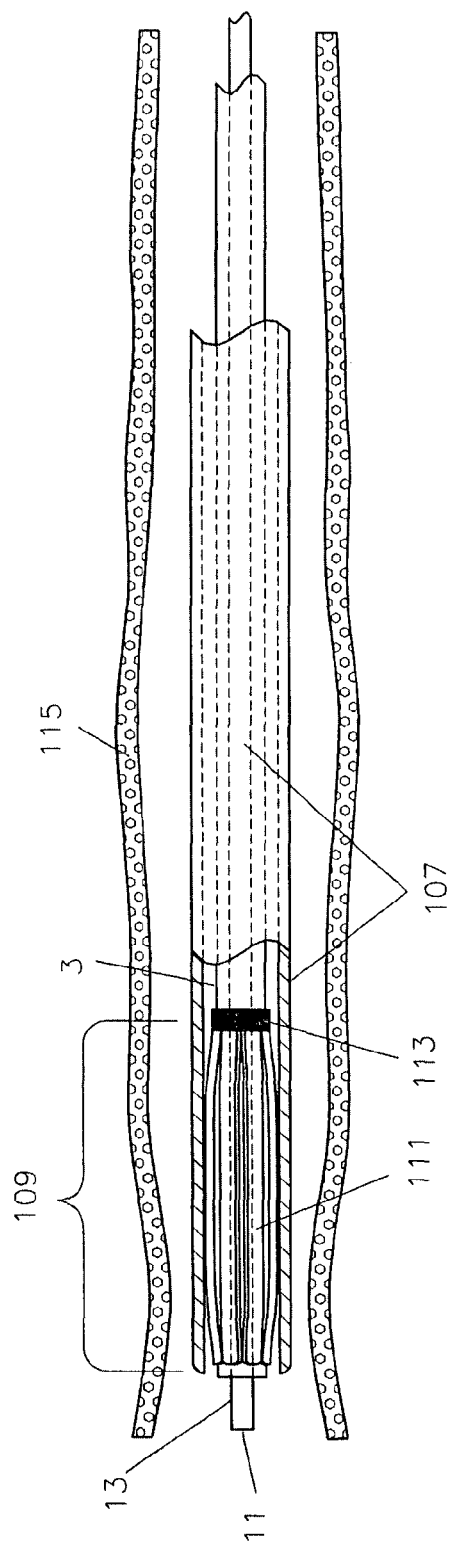
FIG. 14 is a schematic of the distal end of an alternative embodiment of the endovascular laser treatment device within the vein.

Alternative embodiments of a fiber tip spacer according to the invention are illustrated in FIG. 14 through FIG. 17. One variation of the spacer element is depicted in FIG. 14. FIG. 14 is a schematic of an expanding spacer 109 within a retractable sleeve 107 which has been placed into a vein 115. The expanding spacer 109 is comprised of a plurality of spacer ribs 111, or more particularly spacer legs, which are attached to the outer wall of the optical fiber 3 by a circumferential ring 113. Standard bonding or welding techniques well known in the art can be used to affix the circumferential ring 113 to the optical fiber 3 and spacer legs 111. Alternatively, the spacer legs 111 and the circumferential ring 113 can be fabricated as a single unit and then attached to the optical fiber 3.

The spacer legs 111 are pre-curved and preferably made of nitinol or other shape memory type material such as stainless steel or a polymer material. Typically, the expanding spacer 109 is formed of three to six legs 111 although other configurations are possible. The retractable sleeve 107 retains the plurality of legs 111 within their unexpanded and undeployed position around the optical fiber 3. At the distal end of the device, the fiber tip 11 extends beyond the spacer legs 111 by 1-3 cm.

Figure 15:
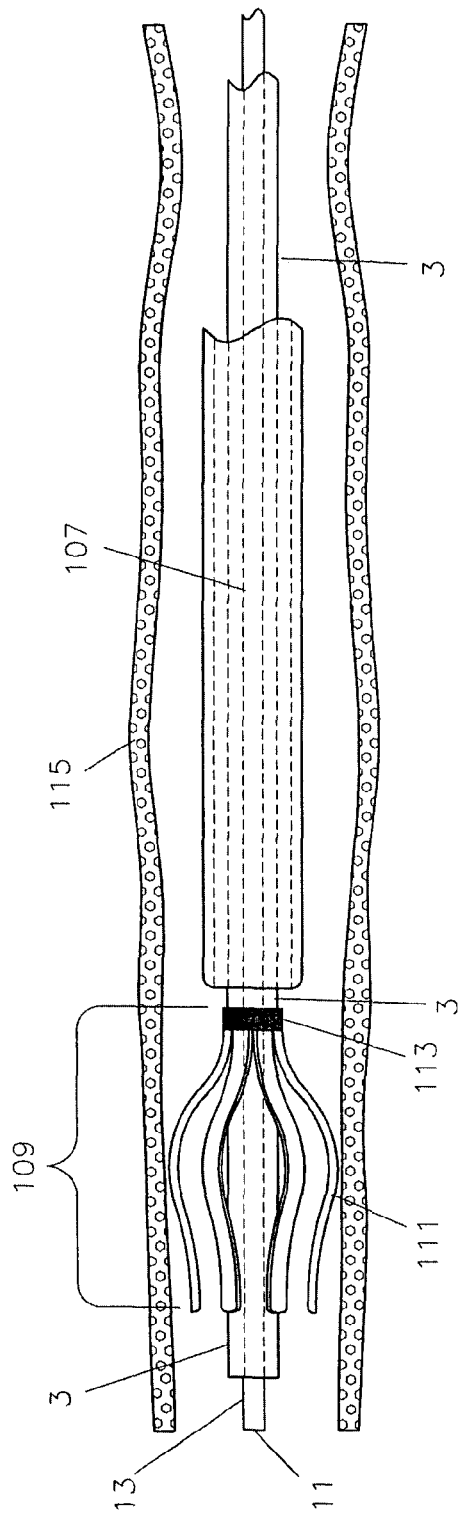
FIG. 15 is a schematic of the FIG. 14 embodiment in the deployed position within the vein.

To deploy the expanding spacer 109, the retractable sleeve 107 is withdrawn while holding the fiber 3 stationary. Any of the previously described deployment configurations can be used to perform the retraction function. Withdrawing the retractable sleeve 107 exposes the spacer legs 111. Due to the shape-memory characteristics of the spacer legs 111, withdrawal of the sleeve 107 causes the spacer legs 111 to expand radially outward to contact the inner vessel wall 115, as shown in FIG. 15. The expanded spacer legs 111 form a cage over the distal end of the device, ensuring that the exposed fiber tip 11 and bare fiber section 13 remain out of contact with the inner wall of the vessel lumen. Similar to the deployed ribs 19 as shown in FIGS. 13A and 13B, complete contact between all spacer legs 111 and the vessel wall is not required. The spacer legs 111 can be deployed such that only some of the legs contact the inner vessel wall and still provide sufficient space to prevent the fiber tip 11 from directly contacting the vessel wall.

If the deployment device 73 of FIG. 5 is used, the amount of radial expansion of the spacer legs 109 can be controlled to accommodate various sizes of the vessels. In addition, in certain cases, it may be advantageous to provide a spacer device that opens sufficiently enough to prevent contact between the fiber tip 11 and vessel wall while minimizing the deployment diameter. Minimizing the deployment diameter of the spacer legs 109 can increase the thermal impact of the gas bubbles on the adjacent vessel wall.

Figure 16:
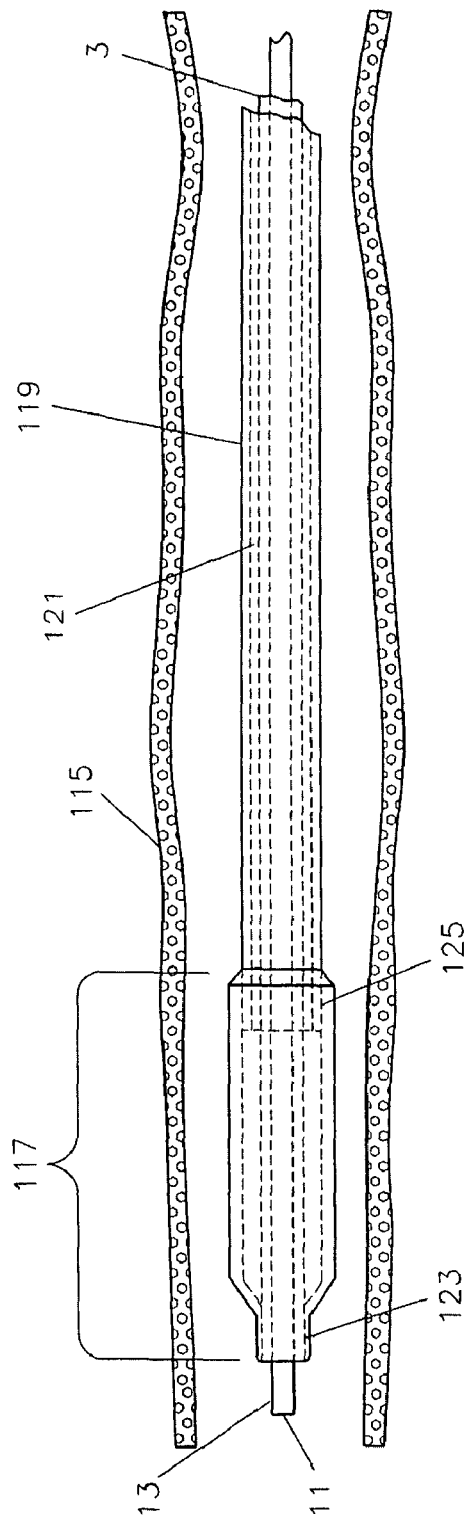
FIG. 16 is a schematic of the distal end of another embodiment of the endovascular laser treatment device in the undeployed position using a balloon mechanism.
Figure 17:
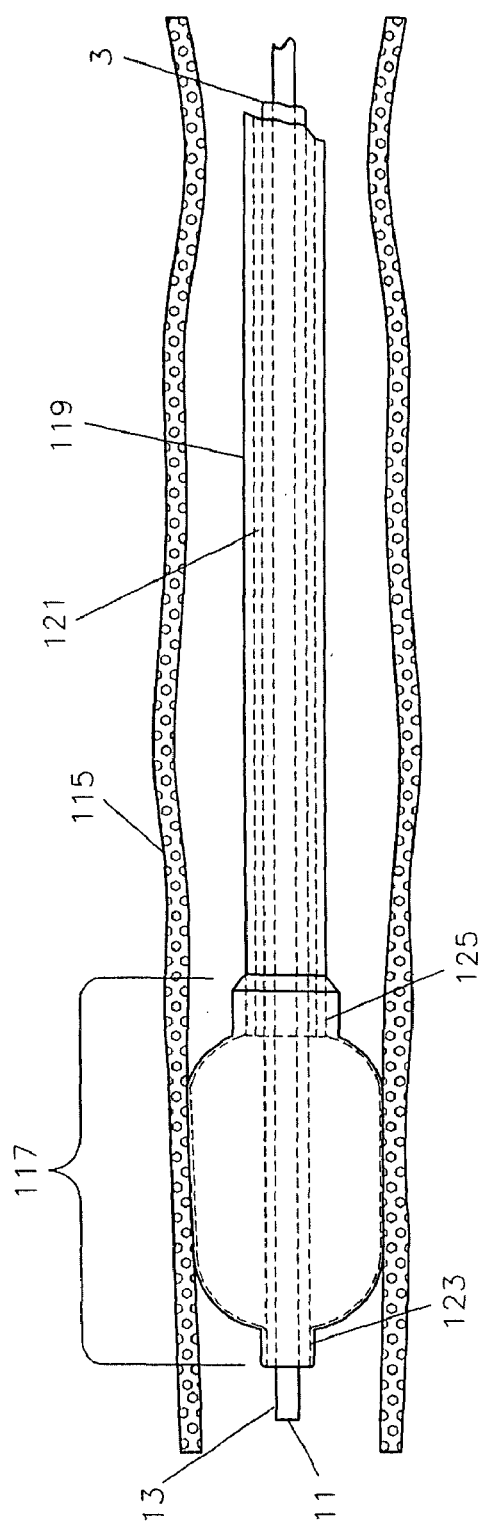
FIG. 17 is a schematic of the FIG. 16 embodiment in the deployed position within the vein.

Referring now to FIG. 16 and FIG. 17, yet another embodiment of the endovascular laser treatment device 1 is disclosed. This embodiment utilizes an expandable balloon assembly to perform the non-contact function. FIG. 16 depicts the balloon 117 assembly in a deflated state within the vein segment 115. The balloon 117 is attached to the fiber 3 at distal bond point 123 and to the outer shaft 119 at proximal bond point 125. The shaft or tube 119 forms a coaxial lumen providing for a balloon inflation/deflation lumen 121. Alternatively, the shaft 119 may be a multi-lumen tube with distinct lumens for the fiber 3 and for the balloon inflation/deflation lumen.

The balloon may be formed from nylon, latex or other similar material well-known in the prior art. The shaft 119 and fiber 3 are inserted and advanced to the treatment location with the balloon 117 in a deflated position as shown in FIG. 16. Prior to activating the laser generator, the balloon 117 is deployed by injecting saline or other fluid through the inflation/deflation lumen 121 into the balloon 117. As fluid fills the balloon 117, it expands to prevent the fiber tip 11 from contacting the inner vessel wall 115 as shown in FIG. 17. The deployed balloon maintains the position of the fiber tip 11 within the vein lumen and away from the vessel wall. Once treatment is complete, the balloon is switched to its undeployed deflated state by withdrawing fluid from the balloon through the inflation/deflation lumen 121 using suction or other standard deflation techniques.

A preferred method of using the endovascular laser treatment device 1 for treating varicose veins will now be described. The treatment procedure begins with the standard pre-operative preparation of the patient as is well known in the laser treatment art. Prior to the laser treatment, the patient's diseased venous segments are marked on the skin surface. Typically, ultrasound guidance is used to map the greater saphenous vein from the sapheno-femoral junction to the popliteal area.

The greater saphenous vein is accessed using a standard Seldinger technique. A small gauge needle is used to puncture the skin and access the vein. A guide wire is advanced into the vein through the lumen of the needle. The needle is then removed leaving the guidewire in place. A hemostasis introducer sheath 49 (as depicted in FIG. 4A) may be introduced into the vein over the guidewire and advanced to 1 to 2 centimeters below the sapheno-femoral junction.

Referring to FIG. 4A, the sheath 49 includes a valve gasket 59 that provides a leak-proof seal to prevent the backflow of blood out the sheath proximal opening while simultaneously allowing the introduction of fibers, guidewires and other interventional devices into the sheath. The valve gasket 59 is made of elastomeric material such as a rubber or latex, as commonly found in the art. The gasket 59 opens to allow insertion of the optical fiber 3 and then seals around the outer sleeve shaft 17. However, the valve gasket 59 does not open in response to pressure from the distal side in order to prevent the back-flow of blood or other fluids. The gasket 59 also prevents air from entering the sheath through the proximal hub opening.

An inner dilator may be coupled with the hemostasis sheath to facilitate insertion and advancement of the sheath through the vein. Position of the sheath is then verified and adjusted if necessary using ultrasound. Once correct positioning is confirmed, the guide wire and dilator, if used, are removed leaving the sheath in place.

Procedural fluids may be flushed through the sheath lumen through the side arm stopcock assembly 61 coupled to the sheath through a sidearm port 57. One commonly administered fluid during an endovascular laser treatment procedure is saline which is used to flush blood from the hemostasis sheath 49 prior to or after insertion of the optical fiber 3/fitting assembly 7. Blood is often flushed from the sheath 49 to prevent the adherence of blood to the flat face tip 11 of the optical fiber 3, which can adversely affect the intensity and direction of the laser energy within the vessel. The sidearm stopcock assembly 61 can also be used to administer emergency drugs directly into the vein.

The distal end of the endovascular laser treatment device 1 is inserted into and is advanced through the sheath 49 until positioned as shown in FIG. 4A. Use of a temporary stop (not shown) slidably connected around the sleeve 17 which is positioned between the male luer connector 27 of the fitting assembly 7 and the sheath connector 63 ensures that the fiber tip 11 position relative to the sheath tip 51 is maintained during any user adjustments. Although pre-measurement or taping of the fiber to the sheath is possible, the temporary stop is preferred because it ensures that the fiber tip 11 is in coaxial alignment with the sheath tip 51.

Once the device is positioned within the vein, the tissue immediately surrounding the diseased vessel segment is subjected to numerous percutaneous injections of a tumescent anesthetic agent. The injections, typically lidocaine with or without epinephrine, are administered along the entire length of the greater saphenous vein using ultrasonic guidance and the markings previously mapped out on the skin surface. The tumescent injections perform several functions. The anesthesia inhibits pain caused from the application of laser energy to the vein. The tumescent injection also provides a barrier between the vessel and the adjacent tissue and nerve structures, which restricts the heat damage to within the vessel and prevents non-target tissue damage.

Once the treating physician has confirmed that the sheath tip 51 is correctly positioned approximately 1-2 centimeters below the saphenous-femoral junction, the device 1 is placed in the deployed position in preparation for the delivery of laser energy to the vein lumen. Specifically, the temporary stop is removed and the sheath is withdrawn until the sheath connector 63 comes into contact with the male luer connector 27 of the fitting assembly 7. The two connectors 63 and 27 are threaded together to attach the sheath 49 to the fitting assembly 7. The retraction of the sheath 49 exposes the fiber tip 11 and the slit zone 21 as shown in FIG. 4B. To deploy the spacer ribs 19 that are in their undeployed state as shown in FIG. 4B, the user holds the fiber 3 stationary while advancing the combined fitting assembly 7/sheath 49 as a unit. This action causes the outer sleeve shaft 17 to advance distally and the ribs 19 to expand radially outward against the vessel wall into their deployed state as shown in FIG. 4C. The positioning element 29 prevents over-expansion of the ribs by contact with the proximal chamber face 67.

The device 1 is now in the operating position, ready to delivery laser energy to the diseased vein. A laser generator (not shown) is connected to the SMA connector 9 of fiber 3 and is activated. The combined sheath 49/endovascular laser treatment device 1 is then slowly withdrawn as a single unit through the vein, preferably at a rate of 1-3 millimeters per second. The laser energy travels down the optical fiber 3, through the tip 11 of the optical fiber 3 and into the vein lumen, where it creates hot bubbles of gas in the bloodstream. The gas bubbles expand to contact the vein wall, along a 360-degree circumference, thus damaging vein wall tissue, and ultimately causing collapse of the vessel.

The laser energy should be directed forward in the bloodstream to create the bubbles of gas. The deployed ribs ensure that the laser energy is directed forward into the bloodstream rather than being mis-directly radially against the vessel wall. Misdirected delivery of laser energy may result in vessel wall perforations where heat is concentrated and incomplete tissue necrosis where insufficient thermal energy is delivered. The endovascular treatment device 1 of the present invention with a fiber tip spacer 19 avoids these problems by preventing contact between the fiber tip 13 and the vessel's inner wall as the device is withdrawn through the vessel.

The procedure for treating the varicose vein is considered to be complete when the desired length of the greater saphenous vein has been exposed to laser energy. Normally, the laser generator is turned off when the fiber tip 11 is approximately 3 centimeters from the access site. The combined sheath 49/endovascular laser treatment device 1 is then removed from the body as a single unit.

The above description and the figures disclose particular embodiments of an endovascular laser treatment device with a non-contact feature. It should be noted that various modifications to the device might be made without departing from the scope of the invention. The spacer element can be of various designs as long as it positions the fiber tip away from the vessel wall when the laser generator is activated. For example, a non-expanding, thin, ceramic-type sleeve bonded to the fiber jacket may be used for the spacer mechanism. The ceramic sleeve extends over and is spaced radially away from the fiber tip to prevent vessel wall contact. Although thin, the ceramic sleeve would provide the necessary barrier between the vessel wall and fiber tip to prevent unequal laser energy delivery.

The method of providing attachment of the fiber assembly connector and the hemostasis valve housing can be accomplished in many ways. The described embodiment depicts a dual thread arrangement, but methods such as snap fits or any other means for providing a secure but releasable connection could be used.

It should be noted that many other methods for deploying and retracting the spacer element could be used. For example, a deployment device could be provided by a rotating sleeve (nut) and thread design where the sleeve could be rotated thereby retracting the sheath and exposing the spacer element.

The diameter size of the optical fiber can also be modified. Although 600-micron diameter optical fibers are most commonly used in endovenous laser treatment of varicose veins, diameters as small as 200 microns, for example, can be used. With a smaller diameter optical fiber, the outer sleeve provides not only the functions previously identified above, but also an increase in overall durability of the device. Specifically, the coaxially mounted sleeve provides added protection and strength to the optical fiber.

The foregoing specific embodiments represent just some of the ways of practicing the present invention. Many other embodiments are possible within the spirit of the invention. Accordingly, the scope of the invention is not limited to the foregoing specification, but instead is given by the appended claims along with their full range of equivalents.

What is claimed is:

1. An endovascular laser treatment device comprising:
a ceramic spacer attached to an optical fiber and arranged near a distal end of the optical fiber, the spacer having an exposed surface capable of contacting an inner wall of a blood vessel to prevent the distal end of the optical fiber from contacting the inner wall of the blood vessel.

2. An endovascular laser treatment device comprising:
an optical fiber operable to be inserted into a blood vessel; and
a ceramic spacer attached to the optical fiber and arranged near a distal end of the optical fiber, the ceramic spacer having an exposed surface capable of contacting an inner wall of a blood vessel to prevent the distal end of the optical fiber from contacting the inner wall of the blood vessel.

3. The endovascular laser treatment device according to claim 2, further comprising a sheath adapted to be inserted into the vessel, wherein the optical fiber and the spacer are adapted to be inserted through the sheath.

4. An endovascular treatment method comprising:
inserting into a blood vessel a spacer arranged near a distal end of an optical fiber, the spacer being a ceramic spacer; and
applying laser energy though the distal end of the optical fiber while longitudinally moving the inserted optical fiber and spacer such that the spacer positions the distal end of the optical fiber away from the inner wall of the vessel to prevent the distal end of the optical fiber from contacting the inner wall of the blood vessel, the application of laser energy causing closure of the blood vessel.

5. The method according to claim 4, after the step of inserting, further comprising deploying the spacer to position the distal end of the optical fiber away from the inner wall of the vessel.

* * * * *

Disclaimer

7,273,478—William M. Appling, Granville, NY (US); Eamonn Hobbs, Queensbury, NY (US). ENDOVASCULAR TREATMENT DEVICE HAVING A FIBER TIP SPACER, Patent dated Sep. 25, 2007. Disclaimer filed Sep. 25, 2007, by the Assignee, AngioDynamics, Inc.

Hereby enter this disclaimer for the complete claims 1, 2 and 3 of said patent.

*(Official Gazette, June 15, 2010)*